United States Patent [19]
Reed et al.

[11] 4,109,383
[45] Aug. 29, 1978

[54] DENTAL IMPLANT BENDER

[76] Inventors: Gerald M. Reed, 660 Valley Rd., Glencoe, Ill. 60022; George E. Carpin, 398 Owen Ct., Prospect Hts., Ill. 60070

[21] Appl. No.: 698,190

[22] Filed: Jun. 21, 1976

[51] Int. Cl.² ............................................ A61C 13/00
[52] U.S. Cl. ...................................... 32/10 A; 32/40 R
[58] Field of Search ................. 72/459, 460, 457, 461; 269/289, 303; 32/40 R, 10 A

[56] References Cited
U.S. PATENT DOCUMENTS

| | | | |
|---|---|---|---|
| 159,918 | 2/1875 | Gleason | 72/460 |
| 314,311 | 3/1885 | Bayrer | 72/461 |
| 337,006 | 3/1886 | Mahon | 72/457 |
| 1,051,356 | 1/1913 | Thomas | 269/303 |
| 2,112,415 | 8/1940 | Butler | 303/42 |

Primary Examiner—Robert Peshock
Attorney, Agent, or Firm—Jacques M. Dulin

[57] ABSTRACT

Apparatus and method for precise bending the head, neck and body portions of metallic endosteal dental implants so that false teeth affixed thereto are properly oriented in the mouth of the patient. The apparatus includes a cam-bearing vise which permits rotational and angular bends of the head and neck portions both within and outside the plane of the body portion of the implant. In addition, a fixed-jaw vise portion of the apparatus permits bending the implant body to conform to the shape of the jaw. A bending lever adapted to fit the head portion of the implants, optionally in combination with one or more pointers and index plates, is used for precise rotational or angular bends of the head with respect to the body.

11 Claims, 4 Drawing Figures

DENTAL IMPLANT BENDER

FIELD

This application is directed to a dental implant bender and method of bending metal dental implants used as anchors for false teeth. More particularly, the apparatus comprises fixed-jaw and movable-jaw vises which are specially designed to permit bending the body, head, and neck portions of the implant in both angular and rotational modes. A bending lever specially adapted to fit implant heads and indexing system for precise angular bending are also provided.

BACKGROUND

Relatively recent developments in replacement of lost, malformed or diseased teeth have included oral implantology—the use of so-called implants to anchor teeth prostheses to the jawbones. Approximately 25 years ago a subperiosteal implant technique was developed. In that technique a metallic "saddle" was devised which fit over the jawbone. The false teeth are anchored to prongs extending from the saddle. The prongs serve as the core of the false tooth. This prong has a head portion of a configuration to insure retention of the false tooth crown.

More recently, the endosteal implant was introduced. These implants are inserted (hammered) or emplaced (in a slot) cut along the ridge crest of the jawbone. These are currently known as the vented or ring-type blade implants, but can also include various pin-types and spiral screw-type implants inserted directly into the jawbone. Typical vented blade type of implants are shown in U.S. Pat. Nos. 3,729,825 and 3,465,441.

As described in those patents, these implants are designed with a tapered implanting blade portion which is adapted to be embedded into the patient's jawbone at the ridge crest. A relatively massive head portion extends upward from the shoulders of the blade and serves as a support upon which the artificial tooth structure is mounted. The head is joined to the shoulder of the body portion by a somewhat thinner neck portion which provides a counterset or shoulder preventing the upward loosening of the artificial tooth structure.

The implants are preferably formed of titanium or Vitallium, but may be of any suitable material that is sterilizable and which does not cause rejection or promote infection of the bone tissue or skin tissue growing into contact therewith.

The primary drawback of the endosteal implant is that its use requires great care and skill by the dentist or oral surgeon. There is the possibility of serious injury to the anatomical structures adjacent the implant area such as sinus cavities, nerves, alveolar canals and adjacent natural tooth structures along or under the ridge crests. The head and neck portion of the implant must project the proper depth from the ridge crest and incised tissue. Improper insertion can result in "overseating" of the implant, that is, driving the blade too deeply into the bone tissue. It is thus possible to perforate a sinus cavity or impinge upon a nerve. If the implant is overseated, it must be withdrawn and a larger one emplaced at a shallower depth.

Another problem is retaining the implant in the proper position for several days during which time bone regeneration takes place to hold the implant sufficiently firmly that cementing of the crown portion of the false teeth can take place. If the implant shifts during this bone ingrowth, the final false teeth prosthesis will not be properly aligned.

Since each tooth is inclined at a somewhat different angle from each other tooth in a full set, and different teeth in different patients are inclined differently, it is important that the head and neck portion be angled properly so that the crown portion of the prosthesis fits properly adjacent to natural teeth and adjacent to the other false teeth. Since the implants are generally made of titanium or Vitallium, they are relatively expensive, costing on the order of $50 to $100 for each implant alone. In addition, the metal is relatively brittle, and improper bending and overstressing can cause the implant to snap at the neck portion between the head and the blade portion during bending, or even subsequently when the crown portion of the prosthesis (false tooth) is mounted thereon, or in place in the patient's mouth.

Likewise, the blade may also be bent in a curve to follow the ridgeline of the jaw before the implant is inserted in the jawbone. Endosteal implants as provided by the manufacturers have planar blades, with one or more heads projecting from the upper shoulder of the blade but lying within the plane of the blade. Depending on where the implant is used in the jaw, the blade may have to be formed into curves of various radii. Likewise, the head may have to be rotated with respect to the plane of the blade. Likewise, the head may be angled in the plane of the blade to one side or the other, or bent outwardly or inwardly from the plane of the blade. All of these angular adjustments depend upon the particular location the implant goes, and the particular configuration of that patient's teeth. Proper fitting is a matter of high skill.

At present, there is no known device which can provide for precise bending required for these surgical implants. Currently, dentists and oral surgeons frequently employ pliers to bend implants. This often results in poorly aligned heads, particularly where adjacent heads on the same blade must be inclined at different angles. In addition, this also leads to breakage of the very expensive implants, or removal and reinsertion of the implants. There is, therefore, a significant need for the implant bender and method of the present invention.

THE INVENTION

OBJECTS

It is among the objects of this invention to provide a dental implant bender and method for the precise bending of the blade, head and neck portions of endosteal dental implants.

It is another object of this invention to provide a special cam-action vise for clamping objects uniformly along their length when placed in the vise.

It is another object of this invention to provide a unitary device which permits bending of dental implant heads with respect to the blades in both angular and rotational modes.

It is another object of this invention to provide vises having fixed jaws which are spaced apart by predetermined thickness to provide for the bending of the blades of dental implants of varying thicknesses.

It is another object of this invention to provide a special angular indexing and bending tool for use with the vises of this invention to provide for precision bending of dental implants.

It is another object of this invention to provide fixed-jaw vises of predetermined spacig and which have a chamfered corner to permit precise arcuate bending of dental implant blades.

It is another object of this invention to provide special dental implant vises which have stainless steel, titanium, Vitallium or other biocompatible metal jaws compatible with dental implant materials.

Still other objects of this invention will be evident from the detailed description and the accompanying drawings.

FIGURES

The drawings illustrate the device and method in various embodiments in which like numbers represent the same or similar parts throughout.

SUMMARY

Figure 1:
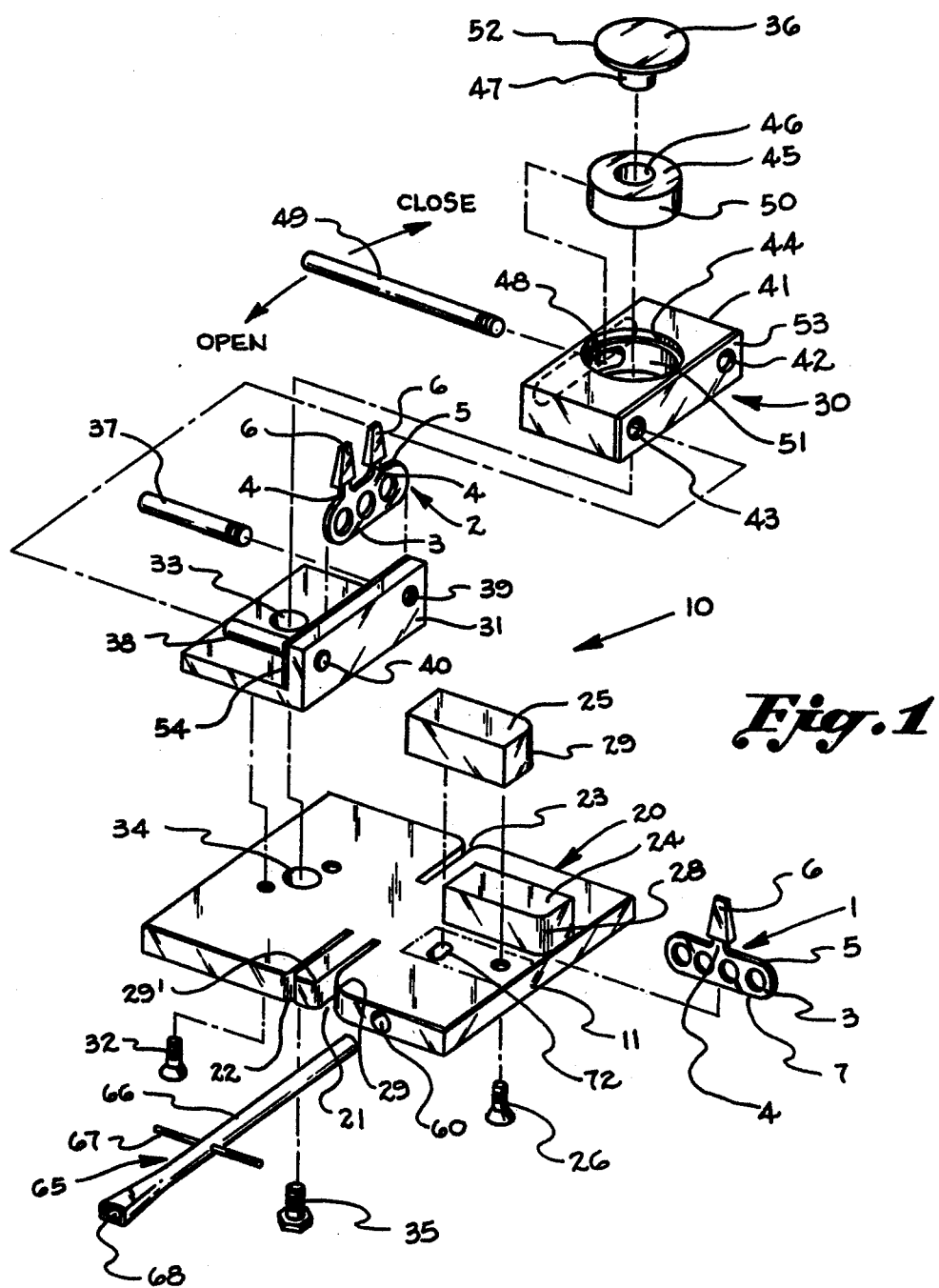
FIG. 1 is an exploded perspective view of the various parts of one embodiment of the dental implant bending device of this invention.

The apparatus of the invention comprises a dental implant bender having one or more movable or fixed-jaw bending vises and a special bending handle adapted to cooperate with the heads of dental implants to facilitate the angular and rotational bending of the head and neck portion of the dental implants relative to the blade. The invention also includes improved methods for bending of dental implants employing the device. Precise bending of the dental implants can be accomplished by use of an indexing member attached to the bending lever. This permits bending of two implants to identical angular or rotational bends, or bending two or more heads on a single dental implant in the same or complementary angles.

The fixed-jaw vise portion of the device comprises one or more pairs of massive jaw units spaced apart a predetermined distance to provide a slot adapted to permit removable retention of the dental implant blade therein. This permits a frictional gripping of the blade, but permits some sliding movement, herein called slidable retention. The slight sliding movement of the blade in the slot during bending assists in producing uniform curves without overstressing the blade. The height of the jaws is matched to that of the dental implant blade. The portion of the blade desired to be bent extends beyond the side face of the jaws permitting simple bending by thumb pressure against a chamfered edge of the jaw. Repeated progressive bending of the blade along its length can provide for precise arcuate bending of the blade along its entire length. A plurality of fixed jaws, or in the alternative, slots in a base member of the device having different spacings to accommodate blades of different thicknesses may be provided. Likewise, the chamfered radius may vary from very small to large to accommodate sharp angular bends or gentle curves.

The movable jaw member comprises a unique cam action vise in which a cam is positioned off-center in one jaw of a movable vise. This cam is actuated by a lever which urges the jaw against a fixed plate comprising the other jaw of the movable vise. The lever action of the movable vise permits firm clamping of the blade along its entire length by parallel compression of the blade between the vise jaw. It is also very easy to operate, and permits tight clamping without crushing by appropriate gauging of the angular motion of the vise lever. The movable jaw is guided by a pair of parallel rods which guide the movable jaw yet provide sufficient play to insure the complete parallel clamping of the dental implant vise along its length.

The bending lever has one end recessed and specifically adapted to receive the head of a dental implant preferably in a telescoping frictional fit. The lever is provided with a cross-piece midway along its length to permit rotational bending. The lever by its length permits angular bending both in the plane and out of the plane of the blade.

The indexing device comprises a clip-on pointer which operates in cooperation with angular position markings inscribed onto one or more faces of the vise. This indexing device permits highly accurate angular bending as well as permitting reproducing the bends for other heads on the same or other dental implant blades. A stowage recess is provided in the base of the device for receivingly engaging the lever so it does not get lost after use.

The implant bender of this invention may be constructed entirely of sterilizable surgical stainless steel, or may employ the stainless steel in combination with titanium or Vitallium facing plates or other biocompatible metals on the jaws of the vises. Providing these metal facings helps prevent contamination of the dental implants with foreign metals, and prevents overstressing of the dental implant due to difference in ductility of the implant as compared to the vise jaws.

DETAILED DESCRIPTION

The following detailed description is by way of example and not by way of limitation of the principles of this invention.

Referring now to FIG. 1, the implant bender device 10 is shown in an exploded perspective view to illustrate the assembly and interrelationship of the parts. It also shows a single-head, vented-type endosteal implant 1 and a double-headed implant 2, the bending manipulation of which is better shown in FIGS. 2 through 4, described below. The implants comprise a generally planar blade portion 3, a neck portion 4 arising from an upper shoulder portion 5, a generally trapezoidal-shaped head 6, and a bottom edge 7. Details of implant construction are not per se part of this invention except as they relate to the bender device being propery adapted to secure them for proper bending. The implants bendable according to the method and device disclosed herein may be of any type, conveniently those shown in U.S. Pat. Nos. 3,465,441 and 3,729,825.

The implant bender device 10 comprises a base plate 11 to which is secured fixed-jaw vise assembly 20 and movable jaw vise assembly 30. The plate may also have slots of varying width and depth 21, 22, and 23 formed therein for securing other implants for storage or for bending. The slots have various widths to accommodate implants having bldes 3 of differing widths. Likewise, the depth may accommodate blades of varying size and configuration such as shown in U.S. Pat. No. 3,729,825.

Figure 2:
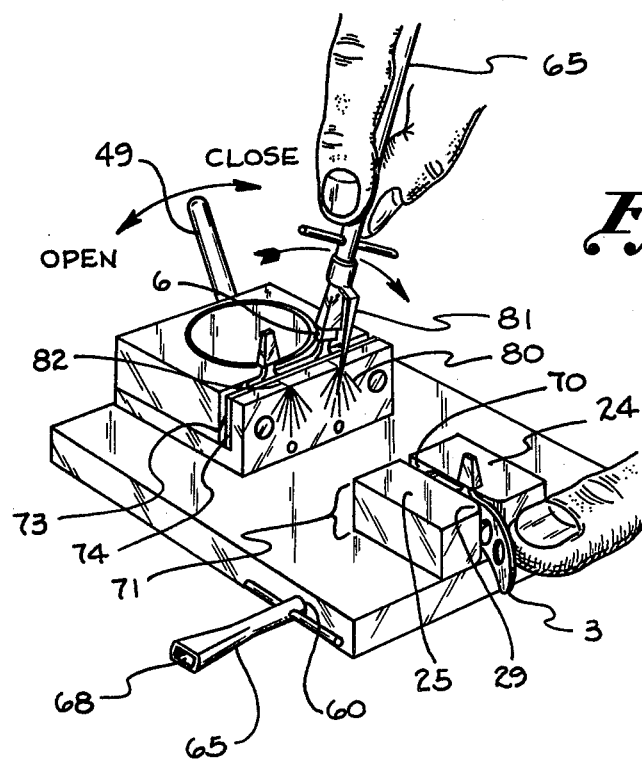
FIG. 2 shows the device of FIG. 1 assembled and illustrates angular bending in the plane of the blade of one dental implant head and neck as well as the bending of the blade of another dental implant in the fixed vise portion of the apparatus.

The fixed-jaw vise assembly 20 comprises a first jaw 24 and a second jaw 25 which are secured to the base plate by any convenient fastening means such as screw 26. The two jaws 24 and 25 are spaced apart from each other by a predetermined thickness to provide for a snug but slidably engageable fit with the blade 3 of the implant 1. In addition, one or more of the jaws 24 and 25 may conveniently have one or both ends rounded or chamfered as at 27 and 28 to provide a surface against which blade 3 may be bent by thumb pressure as best shown in FIG. 2, or by any convenient or desired instrument. As shown in FIG. 1, the chamfer radius 28 of jaw 24 is different from radius 29 of jaw 25 so that different curves may be imparted to the blades simply by reversing the implant in the spacing slot between the two jaws. The curves may be the same radius on each opposing jaws as in the case of the slot 23 or may be of differing radius as at 29 compared to 29' for slot 21. The slot provides a sufficiently snug fit to permit slight lateral movement (in the plane of the blade), by slidable retention, to assist in bending.

The base plate 11 also contains bore 60 in which the bending lever 65 fits snugly for storing. The bending lever 65 comprises a rod 66 with a crosspiece 67 placed medially or at the far end of the rod to assist in rotational bending. In addition, the proximal end of the rod is countersunk as at 68 to provide a snug fit over the generally trapezoidal head 6 of the implant 1. The head-receiving end of the rod may be any shape adapted to fit the various shapes of implant heads now available or which will become available in the future.

The movable jaw vise assembly 30 comprises a fixed jaw portion 31 which is secured to the base 11 by any convenient fastening means such as one or more screws 32. This fixed jaw portion 31 also contains a hole 33 which is aligned with hole 34 in the base plate 11. These holes receive bolt 35 which, with its special threaded cap portion 36, acts as the pivot for cam 45. The fixed jaw portion also has provision for a pair of guide rods 37 and 38 shown threadedly engaged in holes 39 and 40.

A movable jaw portion 41 is provided with a pair of bores 42 and 43 which receive the guide rods 37 and 38. These bores are somewhat larger than the guide rods to provide a reasonable degree of play. The center of the movable jaw is also bored as at 44 to receive cam 45. Bore 44 is sufficiently larger than cam 44 to permit placement of the cam therein in the off-center relationship described below so that its rotation results in reciprocating motion of jaw 41. The cam 45 also contains a bore 46 therethrough for receiving the shank portion 47 of cap 36. The rear of the movable jaw portion 41 is also relieved to provide an oval slot or aperture 48 through which cam lever 49 is secured into a threaded aperture in the backside of the cam (not shown). The movable jaw portion 41 is assembled onto the guide rods 37 and 38. Thereafter, the cam 45 is placed ito its bore 44, and the cam lever is inserted through the oval aperture and threaded into place. The cap shank 47, which has an internally threaded bore for receiving bolt 35, is then placed in the bore 46 in the cam. Thereafter, the bolt 35 is tightened into position. By manipulation of the lever 49 is a horizontally arcuate moton, can surface 50 contacts the bore wall 51 and urges the movable jaw portion along guide rods 37 and 38 in a forward or backward motion, depending on the direction in which the lever 49 is actuated as shown by the arrow A in FIG. 1.

It should be understood that the cam 45 may have an exterior surface 50 concentric with the central bore 46. In this case, the shank 47 is off-center with respect to the center of the flat, circular top 52 of the cap 36. In this embodiment the holes 33 and 34, while themselves aligned and aligned with the shank axis, are not centered with respect to the bore 44 for the cam in the movable jaw portion 41. This off-center relationship of the cam assembly with respect to the bolt bearing assembly 35 and 36, provides for the reciprocating motion of the movable jaw upon actuation of the lever 49.

In another embodiment, central bore 46 of the cam may be off-center with respect to the interior cam surface. The shank of cap 36 is centered with respect to the top, and the holes 33 and 34 are likewise centered with respect to bore 44. The same reciprocating action will result; this is the presently preferred embodiment.

In a still third embodiment, the exterior surface 50 of the cam is not circular, but is eccentric shaped (e.g., an elipse or oval) and provides for the camming action with respect to a centrally oriented bore axially aligned with the centers of apertures 44, 33, and 34.

One or more of the bearing surfaces 53 and 54 of the jaws may be made of titanium, Vitallium, or wironium, the latter two being chrome/cobalt alloys. This permits a matching of materials with the titanium or Vitallium of the implant blades so contamination of the blades with foreign metal particles is avoided. In addition, the compressive and ductile properties of the jaws are matched to that of the blades. However, it should be understood that the entire assembly or any portions thereof may be made of stainless steel, particularly of the type which may be autoclaved or otherwise disinfected. It should also be understood that materials softer than the implant blade material may be used, such as nylon or other material which has the property of resiliency yet can recover its shape upon release of pressure. In practice, matching metal or stainless steel is preferred as it permits totally firm gripping of the blades along the entire length without fractional movement of the blade with respect to the head or the neck upon bending.

Figure 3:
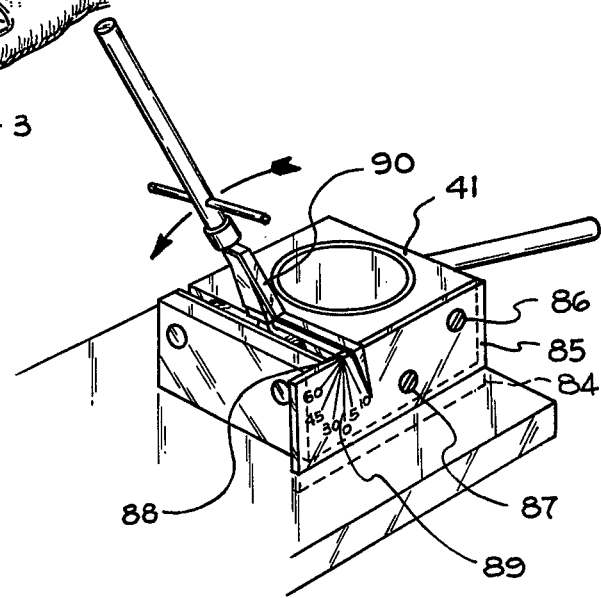
FIG. 3 shows angular bending of the head of the dental implant out of the plane of the blade and illustrates one of the angular indexing devices in use.
Figure 4:
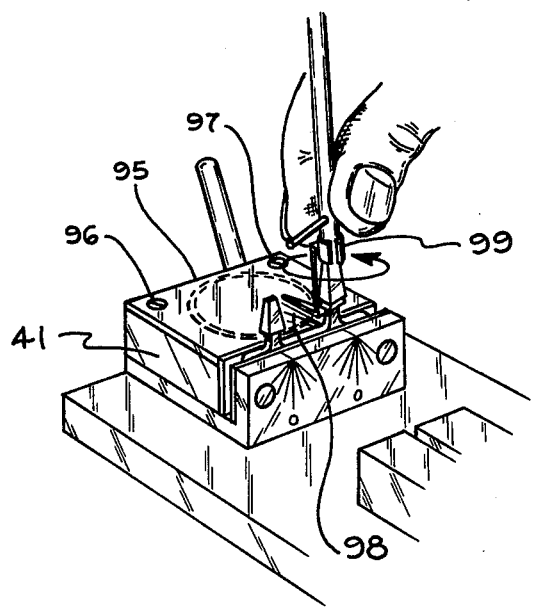
FIG. 4 shows rotational bending of one of the heads of a dual-head dental implant.

Turning now to FIGS. 2 through 4, in operation the device may be used for bending both the blades and the head and neck portion of the implants. In FIG. 2 the bending lever 65 is shown stowed into its receiving bore 60. In addition, the blade 3 of an implant having a single head is shown being bent after placement in the slot 70 between jaws 24 and 25 of the fixed jaw vise portion of the assembly. It can be seen that the chamfered or curved corner of the jaw 29 assists in providing the precise curve desired by providing a surface against which the blade may be bent. The vertical height 71 of the jaw may be approximately equal to the height of the blade between the upper shoulder 5 and the bottom edge 7 but this is not required. It should be understood that while the fixed jaw portions 24 and 25 are fixed, one or more of them may be adjustable by a set screw and slot arrangement (e.g., see slot 72 in FIG. 1) so that blade-retaining slot 70 of an appropriate width may be provided. Optionally, one or more of the corners 73 or 74 may be rounded or chamfered to provide this bending surface.

FIG. 2 also shows the angular bend of a head and neck portion of one head of a two-head implant by use of the bending lever 65. The trapezoidal-shaped bore 68 in one end of the lever is placed over the head 6, and by manipulation of the rod an angular bend to one side or the other from the vertical may be imparted to the head and neck portion. FIG. 2 shows the bending from side to side in the same plane as the blade. A series of indexing lines 80 showing angular displacement in convenient increments, such as from 1°-5° increments, is provided on the exterior face of the movable jaw assembly. To assist in the precise bending, a clip-on type of pointer 81 is provided which is adapted to fit over the shank of the bending lever. In addition, a neck-centering line 82 is provided.

In operation, the cam lever 49 is initially in the open position (see arrow in FIGS. 1 and 2). The implant is inserted between the jaws, and the center of the neck is lined up with the centering line 82. The cam lever 49 is reciprocated (to the right in FIG. 2), firmly clamping the blade along its entire length. Thereafter, the head and neck portion of the implant is bent with the aid of the bending lever 65 and pointer 81.

If the implant blade is canted slightly when the jaws are in the open position, the guide rods 37 and 38 permit enough play in the movable jaw portion 41 of the movable jaw vise to align itself with the exterior face of the blade. Upon reciprocating the cam, the entire blade is brought into parallel alignment with both jaws due to the play permitted. This provides an extremely firm grip with no play and permits precise bending of the implant head and neck portions.

For a dual or triple-head implant, a plurality of the indexing and alignment lines may be provided as shown in FIG. 2.

FIG. 3 illustrates an angular bend of the head and neck portion out of the plane of the blade. In addition, there is provided an indexing plate 85 which is secured to the movable jaw portion 41 of the movable jaw vise by means of appropriate fastening means such as screws 86 and 87. A centering line 88 may be provided approximately in the center of the space between the jaws. As described above for the fixed jaw vise, the indexing plate 85 may be adjusted fore or aft by the provision of oval slots instead of round screw holes in the plate to receive the screws 86 and 87. A series of angularly inclined indexing lines 89 are provided in the indexing plate as shown for forward or aft bending of the head and neck portion out of the plane of the blade. A pointer 90 permits the precise angular bending.

In alternate embodiments, the indexing plate may be secured either to the base plate 11, or to the fixed jaw portion 31 of the movable jaw vise, to permit free movement of the movable jaw portion 41. In still another embodiment, a slot such as 84 (FIG. 3) may be employed to receive the indexing plate 85. The slots are located in the base plate adjacent one or more of the side faces of the vise.

FIG. 4 shows rotational bend of the head and neck portion of an implant. An indexing plate 95 is secured to the top surface of the movable jaw portion 41 of the movable jaw vise. Indexing lines 98 are provided and cooperate with the clip-on pointer 99 to provide for accurate angular bending of the head and neck in a rotational mode.

It should be understood that the head engaging end of the bender may be adapted to accommodate implants of differing head shapes than those shown herein, such as round, square, flat, triangular, etc. Implants of all body types (e.g., vented and solid, tapered, flat, or concave) and all base types (e.g., open and closed) may be bent by the device and method of this invention. Likewise, the guide pins or rods 37, 38 in the movable jaw vise need not be placed to the sides of the cam, but may be placed below the cam. In this embodiment, the edges of the jaws may be rounded as in the fixed jaw vise to assist in the bending of the implant blade.

By use of the above device and the method shown, precise and reproducibly accurate bending of these miniature endosteal dental implants may be accomplished. More precise fitting of the crown portion of the dental prosthesis (the false teeth) can be achieved.

It should be understood that various modifications within the scope of this invention can be made by one of ordinary skill in the art without departing from the spirit thereof. We therefore wish our invention to be defined by the scope of the appended claims as broadly as the prior art will permit, and in view of this specification if need be.

We claim:

1. An apparatus for bending endosteal dental implants having a generally thin planar blade member having a laterally broader dimension than vertical dimension, and having an intermediate neck portion joining said blade member to a head member which is adapted to receive a dental prosthesis, comprising in operative combination:

a. a base member;
   b. a plurality of means for gripping the entire vertical dimension of at least a lateral portion of the generally planar blade member of said implant, said gripping means being adapted to leave the head member and neck portion free for rotational or angular bending;
   c. at least one of said gripping means comprises a movable-jaw vise assembly secured to said base member, said movable-jaw vise assembly includes an internal cam, a cam-actuated jaw adapted to reciprocate relative to a fixed jaw upon rotational motion of said cam, lever means engaging said cam to impart said rotational motion of said cam, and means for reciprocably guiding said jaw into clamping alignment with said fixed jaw;
   d. means for bending said neck relative to said blade so that said head member is oriented in a different angular or a rotational mode, said bending means being adapted to engage said head member while leaving said neck portion free to permit accurate bending thereof;
   e. a second of said gripping means comprises means for removably receiving at least a portion of the blade of said implant to permit arcuate bending of said blade which includes a pair of generally parallel faces in opposed, spaced-apart fixed relationship, the distance apart of said faces being predetermined to provide frictionally resistant but slidable retention of said blade member therebetween.

2. An apparatus as in claim 1 having a plurality of said fixed blade gripping means.

3. An apparatus as in claim 1 wherein said jaw faces are selected from stainless steel, titanium, vitallium, an alloy compatible with said blade and mixtures thereof.

4. An apparatus as in claim 1 wherein said bending means is a rod-like lever having at least one arm adapted to permit imparting rotational torque to said head and having one end adapted to matingly engage said head, and including means for retaining said bending lever when not in use.

5. An apparatus as in claim 4 wherein said rod-shaped lever has at least one arm disposed at an angle to the axis of said lever to provide controllable rotational motion thereto.

6. An apparatus as in claim 4 which includes at least one pointer assembly adapted to be used in association with said bending lever to indicate rotational or angular position of said bending lever, and means for identifying relative angular position of said bending means with respect to an initial alignment position.

7. An apparatus as in claim 6 wherein said angular position identifying means comprises an indexing plate having relative angular position lines thereon.

8. An apparatus as in claim 6 which includes a plurality of pointers removably securable on said bending means, each separately adapted to indicate one of
   i. angular bending of said head into or out of the plane of said blade,
   ii. angular bending of said head from side to side in the plane of said blade, or
   iii. rotational motion of said head on its neck.

9. An apparatus as in claim 6 wherein said second gripping means includes at least one curved surface coextensive with at least one of said parallel faces to provide a surface against which said blade may be bent.

10. Method of bending endosteal dental implants having a head member adapted to receive a dental prosthesis, an intermediate neck joining a generally thin planar blade member having a laterally broader dimension than vertical dimension, comprising the steps of:
   a. clamping the entire vertical dimension of at least a lateral portion of said generally planar blade member so that said head portion and neck member are free;
   b. inserting said head portion into a matingly engageable recess portion of a bending lever;
   c. applying force to said lever in a pre-selected angular to rotational direction by a pre-selected amount to bend said neck member to incline said head in or out of the plane of said blade, or turn said neck member so that said head portion is disposed in a plane perpendicular to said blade plane, and
   d. controlling the turn of incline of said head portion a predetermined amount in relation to angular displacement of said lever as indicated by said pointer referenced to an angle indexing guide.

11. Method of bending the blade portion of an endosteal dental implant comprising the steps of:
   a. inserting one end of said blade into a slot sized to removably frictionally engage said blade; and
   b. applying pressure transversely to the axis of said blade against a curved fulcrum surface disposed oppose to said pressure in an amount sufficient to impart a substantially smooth curve to said blade.

* * * * *

UNITED STATES PATENT AND TRADEMARK OFFICE
CERTIFICATE OF CORRECTION

PATENT NO. : 4,109,383

DATED : August 29, 1978

INVENTOR(S) : Reed et al.

It is certified that error appears in the above-identified patent and that said Letters Patent are hereby corrected as shown below:

Column 2, line 68, "spacig" should read --spacing--.

Column 4, line 7, after "movable" please insert --vise--.

Column 4, line 34, "difference" should read --differences--.

Column 4, line 52, "propery" should read --properly--.

Column 4, line 63, "bldes" should read --blades--.

Column 5, line 54, "ito" should read --into--.

Column 5, line 60, "moton," should read --motion,--.

Column 5, line 60, "can" should read --cam--.

Column 6, line 52, after "7" please insert --,--.

Column 8, line 41, "accurate" should read --arcuate--.

Column 9, line 8, "pluraity" should read --plurality--.

Column 10, line 23, "oppose" should read --opposed--.

Signed and Sealed this

Ninth Day of October 1979

[SEAL]

Attest:

RUTH C. MASON
Attesting Officer

LUTRELLE F. PARKER
Acting Commissioner of Patents and Trademarks